(12) United States Patent
Colmenares et al.

(10) Patent No.: US 10,949,986 B1
(45) Date of Patent: Mar. 16, 2021

(54) METHODS AND SYSTEMS FOR IMAGING A SCENE, SUCH AS A MEDICAL SCENE, AND TRACKING OBJECTS WITHIN THE SCENE

(71) Applicant: Proprio, Inc., Seattle, WA (US)

(72) Inventors: David Julio Colmenares, Seattle, WA (US); James Andrew Youngquist, Seattle, WA (US); Adam Gabriel Jones, Seattle, WA (US); Thomas Ivan Nonn, Kenmore, WA (US); Jay Peterson, Seattle, WA (US)

(73) Assignee: PROPRIO, INC., Seattle, WA (US)

( * ) Notice: Subject to any disclaimer, the term of this patent is extended or adjusted under 35 U.S.C. 154(b) by 0 days.

(21) Appl. No.: 15/930,305

(22) Filed: May 12, 2020

(51) Int. Cl.
| | | |
|---|---|---|
| G06T 11/00 | (2006.01) |
| G06T 7/292 | (2017.01) |
| H04N 5/247 | (2006.01) |
| G06T 7/70 | (2017.01) |
| H04N 5/232 | (2006.01) |
| H04N 5/265 | (2006.01) |
| H04N 5/262 | (2006.01) |
| G06T 7/80 | (2017.01) |
| A61B 90/00 | (2016.01) |
| A61B 34/20 | (2016.01) |

(Continued)

(52) U.S. Cl.
CPC .............. *G06T 7/292* (2017.01); *A61B 34/20* (2016.02); *A61B 90/361* (2016.02); *A61B 90/50* (2016.02); *G06T 7/70* (2017.01); *G06T 7/80* (2017.01); *G06T 11/00* (2013.01); *H04N 5/2253* (2013.01); *H04N 5/23238* (2013.01); *H04N 5/247* (2013.01); *H04N 5/265* (2013.01); *H04N 5/2628* (2013.01); *A61B 2034/2057* (2016.02); *A61B 2090/364* (2016.02); *A61B 2090/371* (2016.02); *G06T 2207/10048* (2013.01); *G06T 2207/30012* (2013.01)

(58) Field of Classification Search
CPC .............................. G06T 7/292; A61B 34/20
See application file for complete search history.

(56) References Cited

U.S. PATENT DOCUMENTS

| | | |
|---|---|---|
| 9,497,380 B1 | 11/2016 | Jannard et al. |
| 9,503,709 B2 | 11/2016 | Shi et al. |

(Continued)

FOREIGN PATENT DOCUMENTS

| | | |
|---|---|---|
| CN | 204854653 U | 12/2015 |
| WO | 2018097831 A1 | 5/2018 |

*Primary Examiner* — Terrell M Robinson
(74) *Attorney, Agent, or Firm* — Perkins Coie LLP

(57) ABSTRACT

Camera arrays for mediated-reality systems and associated methods and systems are disclosed herein. In some embodiments, a camera array includes a support structure having a center, and a depth sensor mounted to the support structure proximate to the center. The camera array can further include a plurality of cameras mounted to the support structure radially outward from the depth sensor, and a plurality of trackers mounted to the support structure radially outward from the cameras. The cameras are configured to capture image data of a scene, and the trackers are configured to capture positional data of a tool within the scene. The image data and the positional data can be processed to generate a virtual perspective of the scene including a graphical representation of the tool at the determined position.

20 Claims, 12 Drawing Sheets

(51) Int. Cl.
*A61B 90/50* (2016.01)
*H04N 5/225* (2006.01)

(56) References Cited

U.S. PATENT DOCUMENTS

| | | | |
|---|---|---|---|
| 2003/0209096 A1* | 11/2003 | Pandey | A61B 34/20 |
| | | | 73/865.9 |
| 2004/0169673 A1* | 9/2004 | Crampe | G06Q 50/22 |
| | | | 715/700 |
| 2006/0203959 A1* | 9/2006 | Spartiotis | H04N 5/23238 |
| | | | 378/38 |
| 2011/0015518 A1* | 1/2011 | Schmidt | A61B 34/10 |
| | | | 600/424 |
| 2013/0076863 A1* | 3/2013 | Rappel | G02B 21/22 |
| | | | 348/46 |
| 2015/0201176 A1 | 7/2015 | Graziosi et al. | |
| 2016/0080734 A1* | 3/2016 | Aguirre-Valencia | |
| | | | G06T 15/20 |
| | | | 348/51 |
| 2016/0352982 A1* | 12/2016 | Weaver | H04N 5/23238 |
| 2017/0007334 A1* | 1/2017 | Crawford | A61B 34/20 |
| 2017/0099479 A1 | 4/2017 | Browd et al. | |
| 2017/0237971 A1 | 8/2017 | Pitts | |
| 2018/0012413 A1* | 1/2018 | Jones | G06T 19/006 |
| 2018/0263707 A1* | 9/2018 | Sela | A61B 5/055 |
| 2018/0293744 A1 | 10/2018 | Yu | |
| 2018/0302572 A1* | 10/2018 | Barnes | G03B 35/08 |
| 2019/0158799 A1 | 5/2019 | Gao et al. | |
| 2019/0289284 A1* | 9/2019 | Smith | A61B 34/20 |
| 2020/0005521 A1 | 1/2020 | Youngquist et al. | |
| 2020/0084430 A1 | 3/2020 | Kalarn et al. | |
| 2020/0105065 A1 | 4/2020 | Youngquist et al. | |
| 2020/0154049 A1* | 5/2020 | Steuart, III | G03B 37/04 |

* cited by examiner

METHODS AND SYSTEMS FOR IMAGING A SCENE, SUCH AS A MEDICAL SCENE, AND TRACKING OBJECTS WITHIN THE SCENE

TECHNICAL FIELD

The present technology generally relates to a camera array, and more specifically, to a camera array for (i) generating a virtual perspective of a scene for a mediated-reality viewer and (ii) tracking objects within the scene.

BACKGROUND

In a mediated reality system, an image processing system adds, subtracts, and/or modifies visual information representing an environment. For surgical applications, a mediated reality system may enable a surgeon to view a surgical site from a desired perspective together with contextual information that assists the surgeon in more efficiently and precisely performing surgical tasks. Such contextual information may include the position of objects within the scene, such as surgical tools. However, it can be difficult to precisely track objects while maintaining low system latency. Moreover, such mediated reality systems rely on multiple camera angles to reconstruct an image of the environment. However, even small relative movements and/or misalignments between the multiple cameras can cause unwanted distortions in the reconstructed image.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

Figure 1:
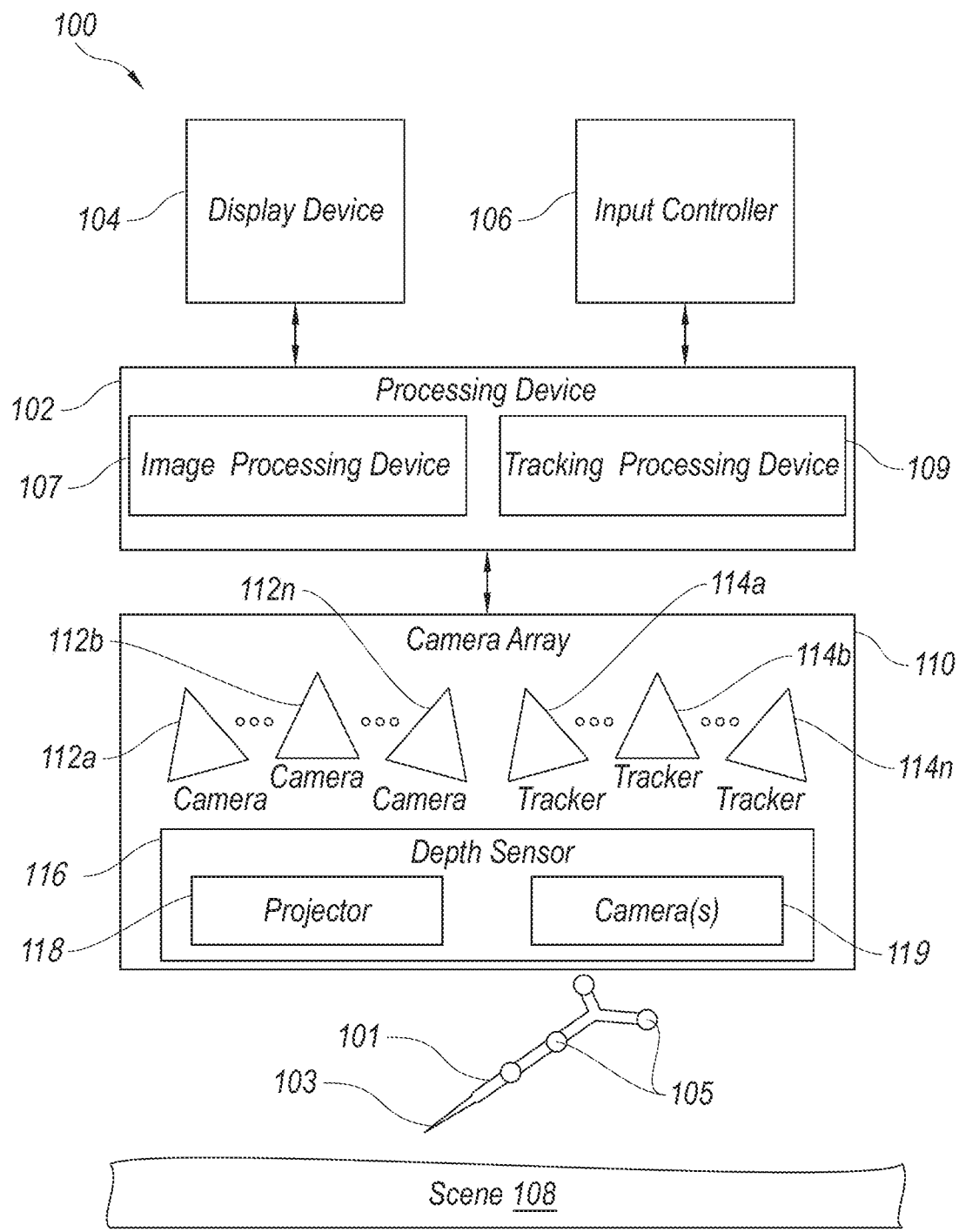
FIG. 1 is a schematic view of an imaging system in accordance with embodiments of the present technology.

Aspects of the present technology are directed generally to mediated-reality imaging systems, such as for use in surgical procedures. In several of the embodiments described below, for example, an imaging system includes a camera array having (i) a depth sensor, (ii) a plurality of cameras, and (iii) a plurality of trackers. The depth sensor, cameras, and trackers can each be mounted to a common frame and positioned within a housing. In some embodiments, the depth sensor is mounted to the frame near a center of the frame. The cameras can be mounted to the frame radially outward from the depth sensor and are configured to capture image data of a scene. In some embodiments, the cameras are high resolution RGB cameras. The trackers can be mounted to the frame radially outward from the cameras and are configured to capture positional data of one or more objects within the scene, such as a surgical tool. In some embodiments, the trackers are infrared imagers configured to image and track reflective markers attached to objects within the scene. Accordingly, in one aspect of the present technology the camera array can include a camera system and an optical tracking system integrated onto a common frame.

The imaging system can further include a processing device communicatively coupled to the camera array. The processing device can be configured to synthesize a virtual image corresponding to a virtual perspective of the scene based on the image data from at least a subset of the cameras. The processing device can further determine a position of objects in the scene based on the positional data from at least a subset of the trackers. In some embodiments, the imaging system can further include a display device configured to display a graphical representation of the objects at the determined positions in the virtual image.

In some embodiments, the imaging system is configured to track a tool tip in the scene using data from both the trackers and the cameras. For example, the imaging system can estimate a three-dimensional (3D) position of the tool tip based on the positional data from the trackers. The imaging system can then project the estimated 3D position into two-dimensional (2D) images from the cameras, and define a region of interest (ROI) in each of the images based on the projected position of the tool tip. Then, the imaging system can process the image data in the ROI of each image to determine the location of the tool tip in the ROI. Finally, the tool tip positions determined in the ROIs of the images can be triangulated (or otherwise mapped to the 3D space) to determine an updated, higher precision position of the tool tip.

In one aspect of the present technology, the position of the tool tip determined from the camera data can be more precise than the position determined from the trackers alone, because the cameras have a higher resolution than the trackers. In another aspect of the present technology, the tracking can be done at a high framerate and with low latency because only the ROIs in the images from the cameras need to be processed—rather than the entire images—because the 3D estimate of the position of the tool tip from the trackers is used to initialize the ROIs. Without using the ROIs, the processing requirements for the images from the cameras would be very large and would be difficult or impossible to process with low latency.

Specific details of several embodiments of the present technology are described herein with reference to FIGS. 1-9B. The present technology, however, can be practiced without some of these specific details. In some instances, well-known structures and techniques often associated with camera arrays, light field cameras, image reconstruction, object tracking, etc., have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying figures depict embodiments of the present technology and are not intended to be limiting of its scope. The sizes of various depicted elements are not necessarily drawn to scale, and these various elements can be arbitrarily enlarged to improve legibility. Component details can be abstracted in the figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

The headings provided herein are for convenience only and should not be construed as limiting the subject matter disclosed.

I. Selected Embodiments of Imaging Systems

FIG. 1 is a schematic view of an imaging system 100 ("system 100") in accordance with embodiments of the present technology. In some embodiments, the system 100 can be a synthetic augmented reality system, a mediated-reality imaging system, and/or a computational imaging system. In the illustrated embodiment, the system 100 includes a processing device 102 that is operably/communicatively coupled to one or more display devices 104, one or more input controllers 106, and a camera array 110. In other embodiments, the system 100 can comprise additional, fewer, or different components. In some embodiments, the system 100 can include some features that are generally similar or identical to those of the imaging systems disclosed in U.S. patent application Ser. No. 16/586,375, titled "CAMERA ARRAY FOR A MEDIATED-REALITY SYSTEM," file Sep. 27, 2019, which is incorporated herein by reference in its entirety.

In the illustrated embodiment, the camera array 110 includes a plurality of cameras 112 (identified individually as cameras 112a-112n) that are each configured to capture images of a scene 108 from a different perspective. The camera array 110 further includes a plurality of dedicated object trackers 114 (identified individually as trackers 114a-114n) configured to capture positional data of one more objects, such as a tool 101 (e.g., a surgical tool) having a tip 103, to track the movement and/or orientation of the objects through/in the scene 108. In some embodiments, the cameras 112 and the trackers 114 are positioned at fixed locations and orientations (e.g., poses) relative to one another. For example, the cameras 112 and the trackers 114 can be structurally secured by/to a mounting structure (e.g., a frame) at predefined fixed locations and orientations (e.g., as described in further detail below with reference to FIGS. 3A-5C). In some embodiments, the cameras 112 can be positioned such that neighboring cameras 112 share overlapping views of the scene 108. Likewise, the trackers 114 can be positioned such that neighboring trackers 114 share overlapping views of the scene 108. Therefore, all or a subset of the cameras 112 and the trackers 114 can have different extrinsic parameters, such as position and orientation.

In some embodiments, the cameras 112 in the camera array 110 are synchronized to capture images of the scene 108 substantially simultaneously (e.g., within a threshold temporal error). In some embodiments, all or a subset of the cameras 112 can be light-field/plenoptic/RGB cameras that are configured to capture information about the light field emanating from the scene 108 (e.g., information about the intensity of light rays in the scene 108 and also information about a direction the light rays are traveling through space). Therefore, in some embodiments the images captured by the cameras 112 can encode depth information representing a surface geometry of the scene 108. In some embodiments, the cameras 112 are substantially identical. In other embodiments, the cameras 112 can include multiple cameras of different types. For example, different subsets of the cameras 112 can have different intrinsic parameters such as focal length, sensor type, optical components, etc. The cameras 112 can have charge-coupled device (CCD) and/or complementary metal-oxide semiconductor (CMOS) image sensors and associated optics. Such optics can include a variety of configurations including lensed or bare individual image sensors in combination with larger macro lenses, micro-lens arrays, prisms, and/or negative lenses.

In some embodiments, the trackers 114 are imaging devices, such as infrared (IR) cameras that are each configured to capture images of the scene 108 from a different perspective compared to other ones of the trackers 114. Accordingly, the trackers 114 and the cameras 112 can have different spectral sensitives (e.g., infrared vs. visible wavelength). In some embodiments, the trackers 114 are configured to capture image data of a plurality of optical markers (e.g., fiducial markers, marker balls, etc.) in the scene 108, such as markers 105 coupled to the tool 101.

In the illustrated embodiment, the camera array 110 further includes a depth sensor 116. In some embodiments, the depth sensor 116 includes (i) one or more projectors 118 configured to project a structured light pattern onto/into the scene 108, and (ii) one or more cameras 119 (e.g., a pair of the cameras 119) configured to detect the structured light projected onto the scene 108 by the projector 118 to estimate a depth of a surface in the scene 108. The projector 118 and the cameras 119 can operate in the same wavelength and, in some embodiments, can operate in a wavelength different than the trackers 114 and/or the cameras 112. In other embodiments, the depth sensor 116 and/or the cameras 119 can be separate components that are not incorporated into an integrated depth sensor. In yet other embodiments, the depth sensor 116 can include other types of dedicated depth detection hardware such as a LiDAR detector, to estimate the surface geometry of the scene 108. In other embodiments, the camera array 110 can omit the projector 118 and/or the depth sensor 116.

In the illustrated embodiment, the processing device 102 includes an image processing device 107 (e.g., an image processor, an image processing module, an image processing unit, etc.) and a tracking processing device 109 (e.g., a tracking processor, a tracking processing module, a tracking processing unit, etc.). The image processing device 107 is configured to (i) receive images (e.g., light-field images, light field image data, etc.) captured by the cameras 112 of the camera array 110 and (ii) process the images to synthesize an output image corresponding to a selected virtual camera perspective. In the illustrated embodiment, the output image corresponds to an approximation of an image of the scene 108 that would be captured by a camera placed at an arbitrary position and orientation corresponding to the virtual camera perspective. In some embodiments, the image processing device 107 is further configured to receive depth information from the depth sensor 116 and/or calibration data to synthesize the output image based on the images, the depth information, and/or the calibration data. More specifically, the depth information and calibration data can be used/combined with the images from the cameras 112 to synthesize the output image as a 3D (or stereoscopic 2D) rendering of the scene 108 as viewed from the virtual camera perspective. In some embodiments, the image processing device 107 can synthesize the output image using any of the methods disclosed in U.S. patent application Ser. No. 16/457,780, titled "SYNTHESIZING AN IMAGE FROM A VIRTUAL PERSPECTIVE USING PIXELS FROM A PHYSICAL IMAGER ARRAY WEIGHTED BASED ON DEPTH ERROR SENSITIVITY," filed Jun. 28, 2019, which is incorporated herein by reference in its entirety.

The image processing device 107 can synthesize the output image from images captured by a subset (e.g., two or more) of the cameras 112 in the camera array 110, and does not necessarily utilize images from all of the cameras 112. For example, for a given virtual camera perspective, the processing device 102 can select a stereoscopic pair of images from two of the cameras 112 that are positioned and oriented to most closely match the virtual camera perspective. In some embodiments, the image processing device 107 (and/or the depth sensor 116) is configured to estimate a depth for each surface point of the scene 108 relative to a common origin and to generate a point cloud and/or 3D mesh that represents the surface geometry of the scene 108. For example, in some embodiments the cameras 119 of the depth sensor 116 can detect the structured light projected onto the scene 108 by the projector 118 to estimate depth information of the scene 108. In some embodiments, the image processing device 107 can estimate depth from multiview image data from the cameras 112 using techniques such as light field correspondence, stereo block matching, photometric symmetry, correspondence, defocus, block matching, texture-assisted block matching, structured light, etc., with or without utilizing information collected by the depth sensor 116. In other embodiments, depth may be acquired by a specialized set of the cameras 112 performing the aforementioned methods in another wavelength.

In some embodiments, the tracking processing device 109 can process positional data captured by the trackers 114 to track objects (e.g., the tool 101) within the vicinity of the scene 108. For example, the tracking processing device 109 can determine the position of the markers 105 in the 2D images captured by two or more of the trackers 114, and can compute the 3D position of the markers 105 via triangulation of the 2D positional data. More specifically, in some embodiments the trackers 114 include dedicated processing hardware for determining positional data from captured images, such as a centroid of the markers 105 in the captured images. The trackers 114 can then transmit the positional data to the tracking processing device 109 for determining the 3D position of the markers 105. In other embodiments, the tracking processing device 109 can receive the raw image data from the trackers 114. In a surgical application, for example, the tracked object may comprise a surgical instrument, a hand or arm of a physician or assistant, and/or another object having the markers 105 mounted thereto. In some embodiments, the processing device 102 may recognize the tracked object as being separate from the scene 108, and can apply a visual effect to distinguish the tracked object such as, for example, highlighting the object, labeling the object, or applying a transparency to the object.

In some embodiments, functions attributed to the processing device 102, the image processing device 107, and/or the tracking processing device 109 can be practically implemented by two or more physical devices. For example, in some embodiments a synchronization controller (not shown) controls images displayed by the projector 118 and sends synchronization signals to the cameras 112 to ensure synchronization between the cameras 112 and the projector 118 to enable fast, multi-frame, multi-camera structured light scans. Additionally, such a synchronization controller can operate as a parameter server that stores hardware specific configurations such as parameters of the structured light scan, camera settings, and camera calibration data specific to the camera configuration of the camera array 110. The synchronization controller can be implemented in a separate physical device from a display controller that controls the display device 104, or the devices can be integrated together.

The processing device 102 can comprise a processor and a non-transitory computer-readable storage medium that stores instructions that when executed by the processor, carry out the functions attributed to the processing device 102 as described herein. Although not required, aspects and embodiments of the present technology can be described in the general context of computer-executable instructions, such as routines executed by a general-purpose computer, e.g., a server or personal computer. Those skilled in the relevant art will appreciate that the present technology can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The present technology can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The present technology can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or sub-routines can be located in both local and remote memory storage devices. Aspects of the present technology described below can be stored or distributed on computer-readable media, including magnetic and optically readable and removable computer discs, stored as in chips (e.g., EEPROM or flash memory chips). Alternatively, aspects of the present technology can be distributed electronically over the Internet or over other networks (including wireless networks). Those skilled in the relevant art will recognize that portions of the present technology can reside on a server computer, while corresponding portions reside on a client computer. Data structures and transmission of data particular to aspects of the present technology are also encompassed within the scope of the present technology.

The virtual camera perspective can be controlled by an input controller 106 that provides a control input corresponding to the location and orientation of the virtual camera perspective. The output images corresponding to the virtual camera perspective are outputted to the display device 104. The display device 104 is configured to receive the output images (e.g., the synthesized three-dimensional rendering of the scene 108) and to display the output images for viewing by one or more viewers. The processing device 102 can process received inputs from the input controller 106 and process the captured images from the camera array 110 to generate output images corresponding to the virtual perspective in substantially real-time as perceived by a viewer of the display device 104 (e.g., at least as fast as the framerate of the camera array 110). Additionally, the display device 104 can display a graphical representation of any tracked objects within the scene 108 (e.g., the tool 101) on/in the image of the virtual perspective.

The display device 104 can comprise, for example, a head-mounted display device, a monitor, a computer display, and/or another display device. In some embodiments, the input controller 106 and the display device 104 are integrated into a head-mounted display device and the input controller 106 comprises a motion sensor that detects position and orientation of the head-mounted display device. The virtual camera perspective can then be derived to correspond to the position and orientation of the head-mounted display device 104 in the same reference frame and at the calculated depth (e.g., as calculated by the depth sensor 116) such that the virtual perspective corresponds to a perspective that would be seen by a viewer wearing the head-mounted display device 104. Thus, in such embodiments the head-mounted display device 104 can provide a real-time rendering of the scene 108 as it would be seen by an observer without the head-mounted display device 104. Alternatively, the input controller 106 can comprise a user-controlled control device (e.g., a mouse, pointing device, handheld controller, gesture recognition controller, etc.) that enables a viewer to manually control the virtual perspective displayed by the display device 104.

Figure 2:
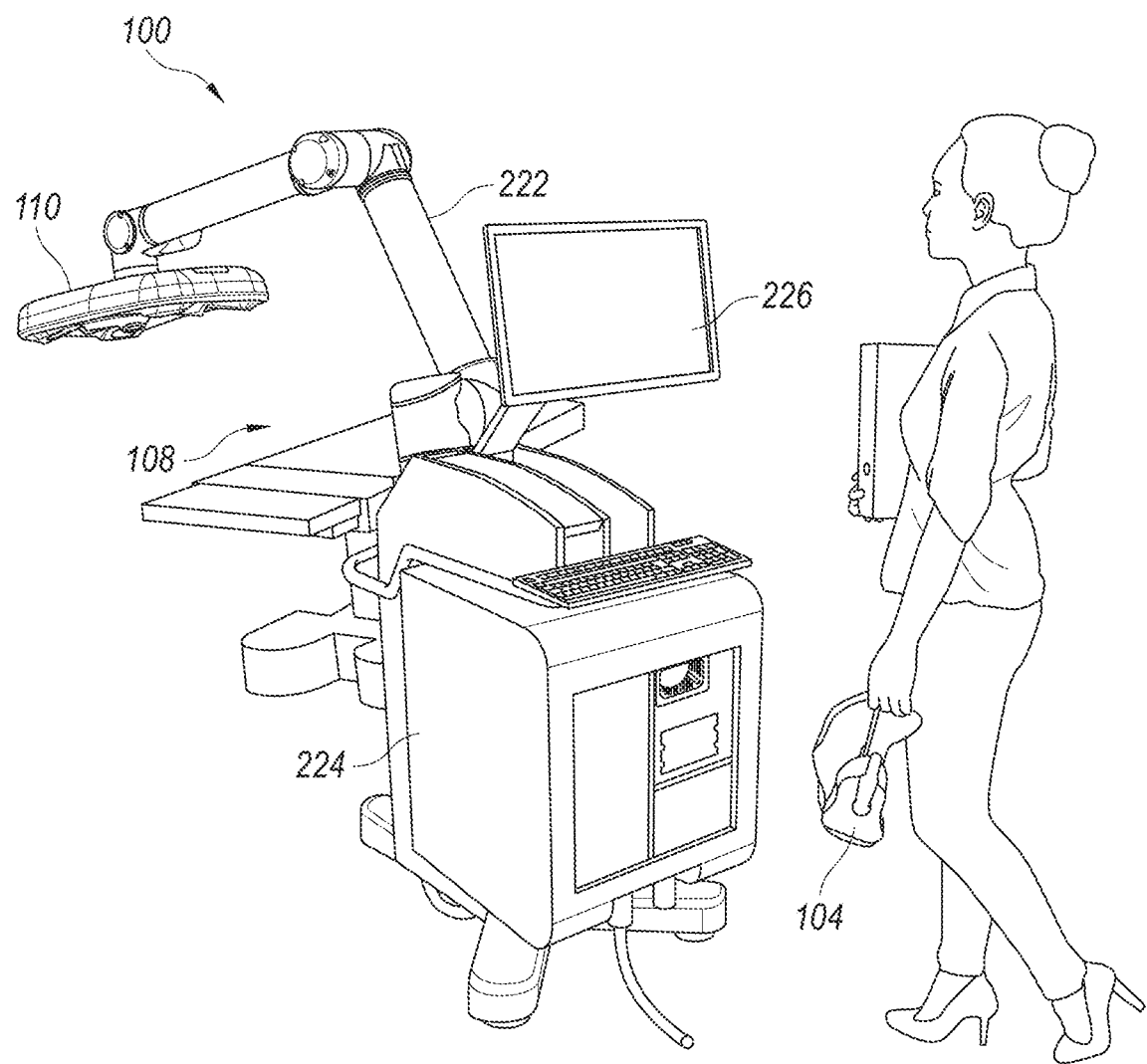
FIG. 2 is a perspective view of a surgical environment employing the imaging system for a surgical application in accordance with embodiments of the present technology.

FIG. 2 is a perspective view of a surgical environment employing the system 100 for a surgical application in accordance with embodiments of the present technology. In the illustrated embodiment, the camera array 110 is positioned over the scene 108 (e.g., a surgical site) and supported/positioned via a movable arm 222 that is operably coupled to a workstation 224. In some embodiments, the arm 222 can be manually moved to position the camera array 110 while, in other embodiments, the arm 222 can be robotically controlled in response to the input controller 106 (FIG. 1) and/or another controller. In the illustrated embodiment, the display device 104 is a head-mounted display device (e.g., a virtual reality headset, augmented reality headset, etc.). The workstation 224 can include a computer to control various functions of the processing device 102, the display device 104, the input controller 106, the camera array 110, and/or other components of the system 100 shown in FIG. 1. Accordingly, in some embodiments the processing device 102 and the input controller 106 are each integrated in the workstation 224. In some embodiments, the workstation 224 includes a secondary display 226 that can display a user interface for performing various configuration functions, a mirrored image of the display on the display device 104, and/or other useful visual images/indications.

II. Selected Embodiments of Camera Arrays

Figure 3A:
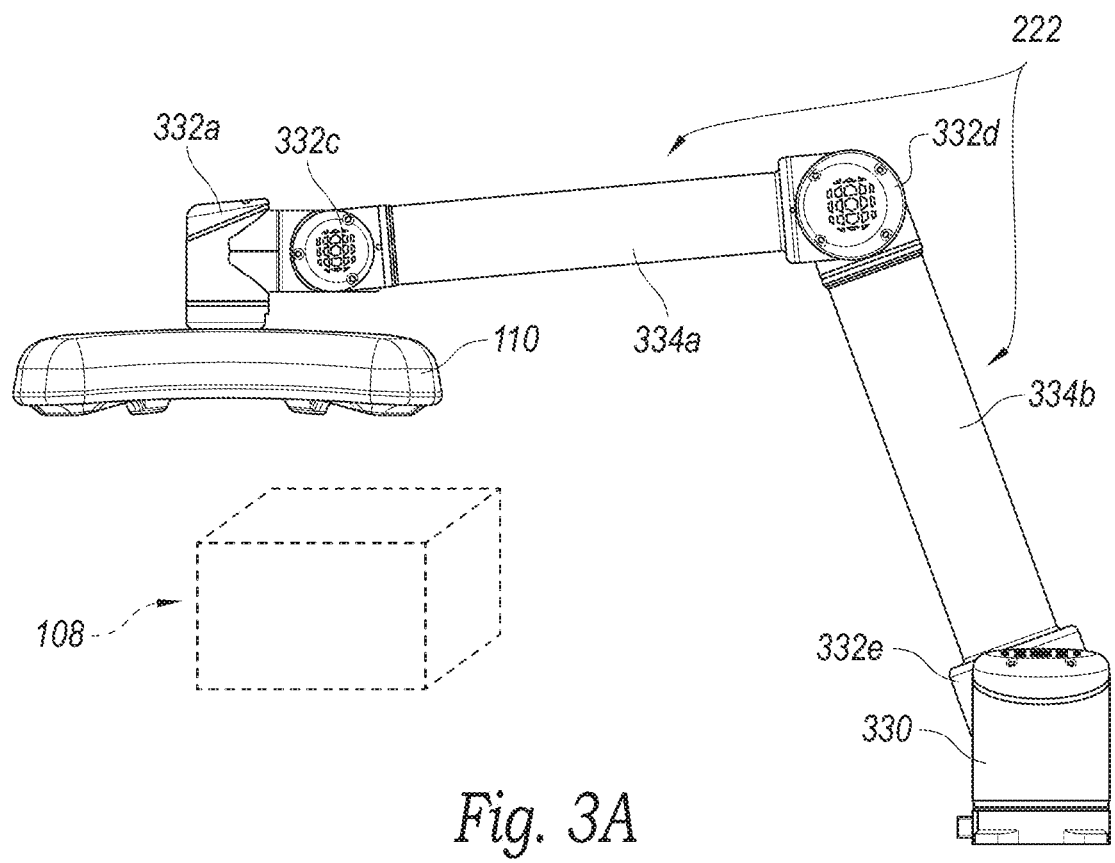
FIGS. 3A and 3B are a side view and an isometric view, respectively, of a camera array and a movable arm of the imaging system in accordance with embodiments of the present technology.
Figure 3B:
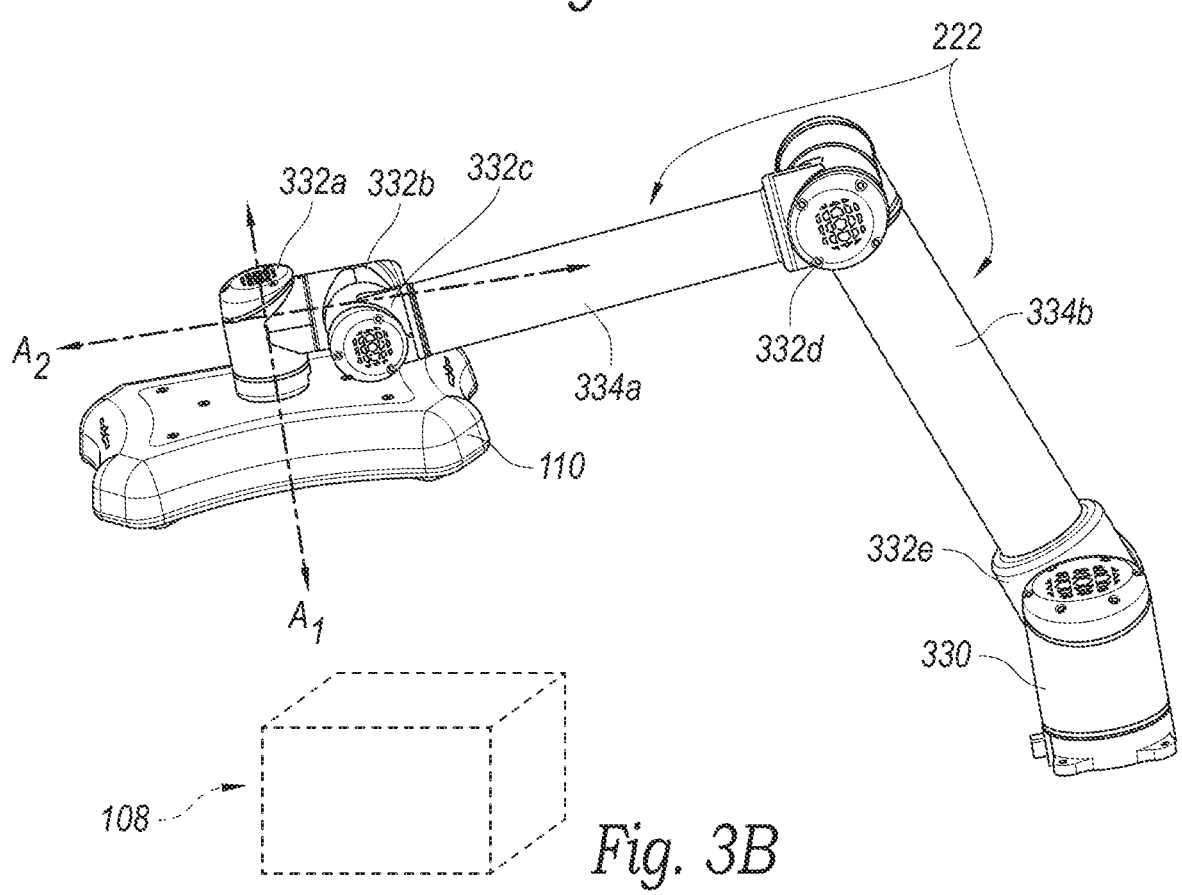

FIGS. 3A and 3B are a side view and an isometric view, respectively, of the camera array 110 and the arm 222 of FIGS. 1 and 2 in accordance with embodiments of the present technology. Referring to FIGS. 3A and 3B together, in the illustrated embodiment the camera array 110 is movably coupled to a base 330 via a plurality of rotatable joints 332 (identified individually as first through fifth joints 332a-332e, respectively) and elongate portions 334 (identified individually as a first elongate portion 334a and a second elongate portion 334b). The base 330 can be securely mounted at a desired location, such as within an operating room (e.g., to a floor or other rigid portion of the operating room), to a movable dolly/cart, etc. The joints 332 allow the camera array 110 to be articulated and/or rotated relative to the scene 108 such that the cameras 112 and the trackers 114 (FIG. 1) can be positioned to capture data of different portions/volumes of the scene 108. Referring to FIG. 3B, for example, the first joint 332a allows the camera array 110 to rotate about an axis $A_1$, the second joint 332b allows the camera array 110 to rotate about an axis $A_2$, and so on. The joints 332 can be controlled manually (e.g., by a surgeon, operator, etc.) or robotically. In some embodiments, the arm 222 has more than three degrees of freedom such that the arm 222 can be positioned at any selected orientation/position relative to the scene 108. In other embodiments, the arm 222 can include more or fewer of the joints 332 and/or the elongate portions 334.

Figure 4A:
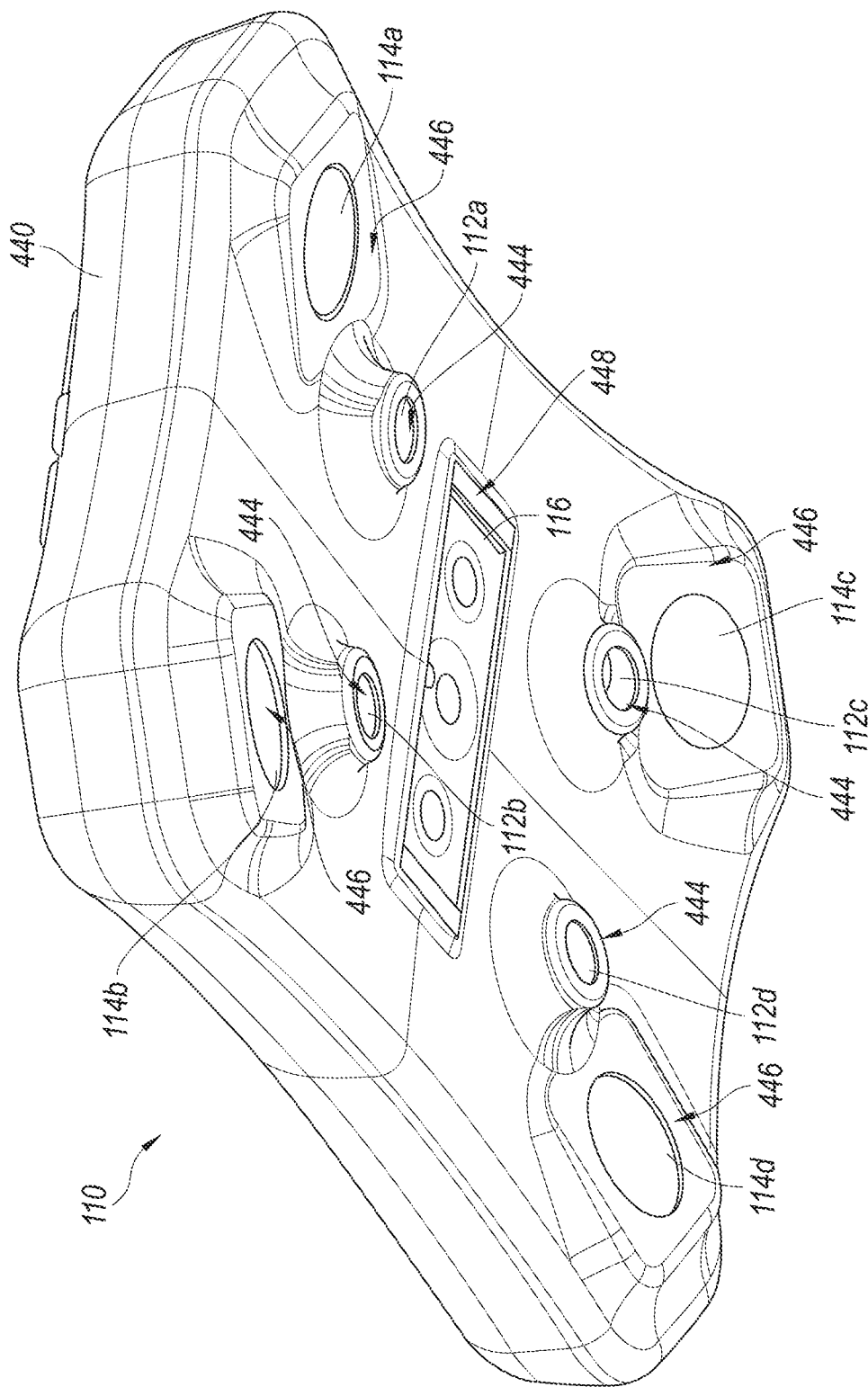
FIGS. 4A-4C are an isometric view, a bottom view, and a side view, respectively, of the camera array in accordance with embodiments of the present technology.
Figure 4B:
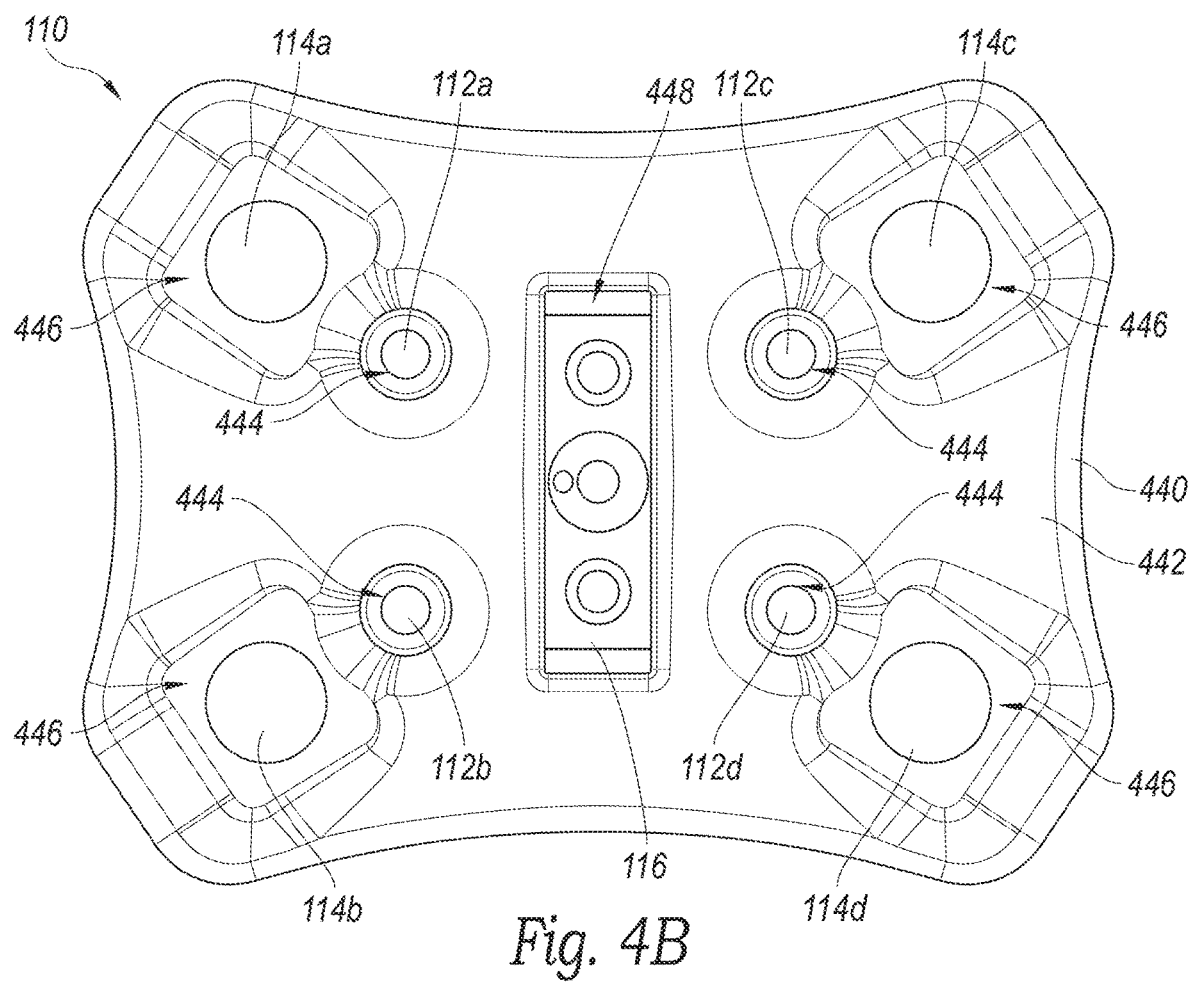
Figure 4C:
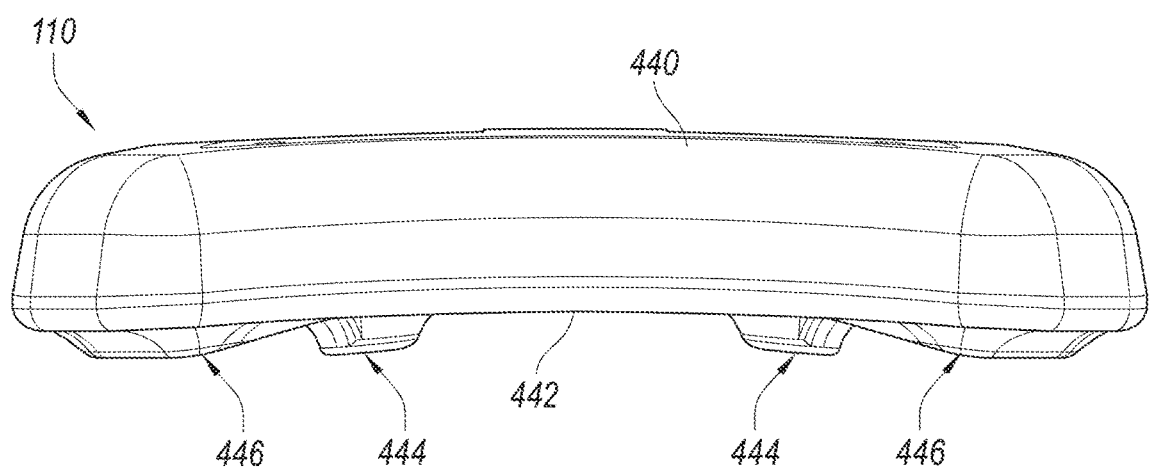
Figure 5A:
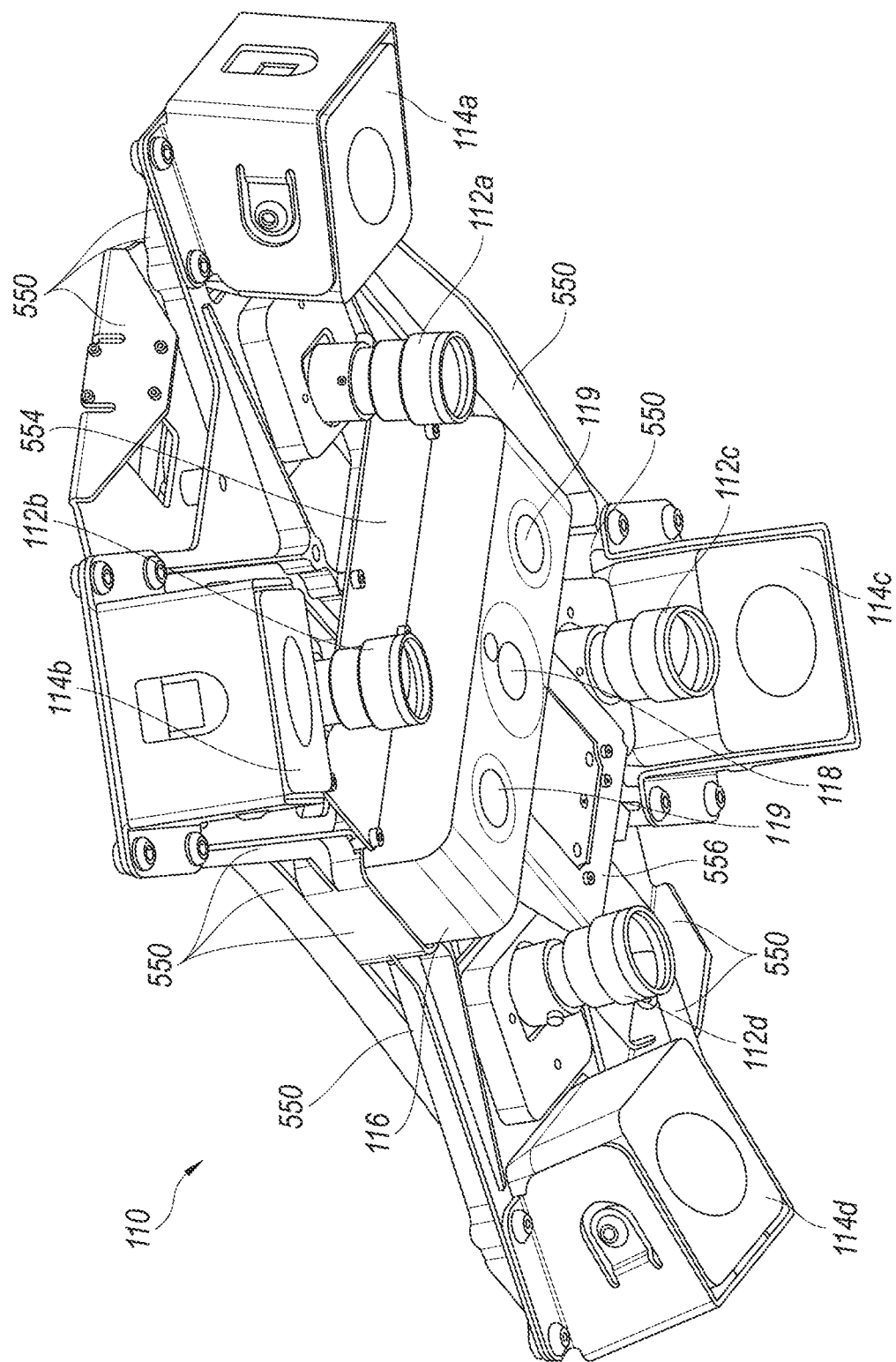
FIGS. 5A-5C are an isometric view, a bottom view, and a side view, respectively, of the camera array with a housing removed in accordance with embodiments of the present technology.
Figure 5B:
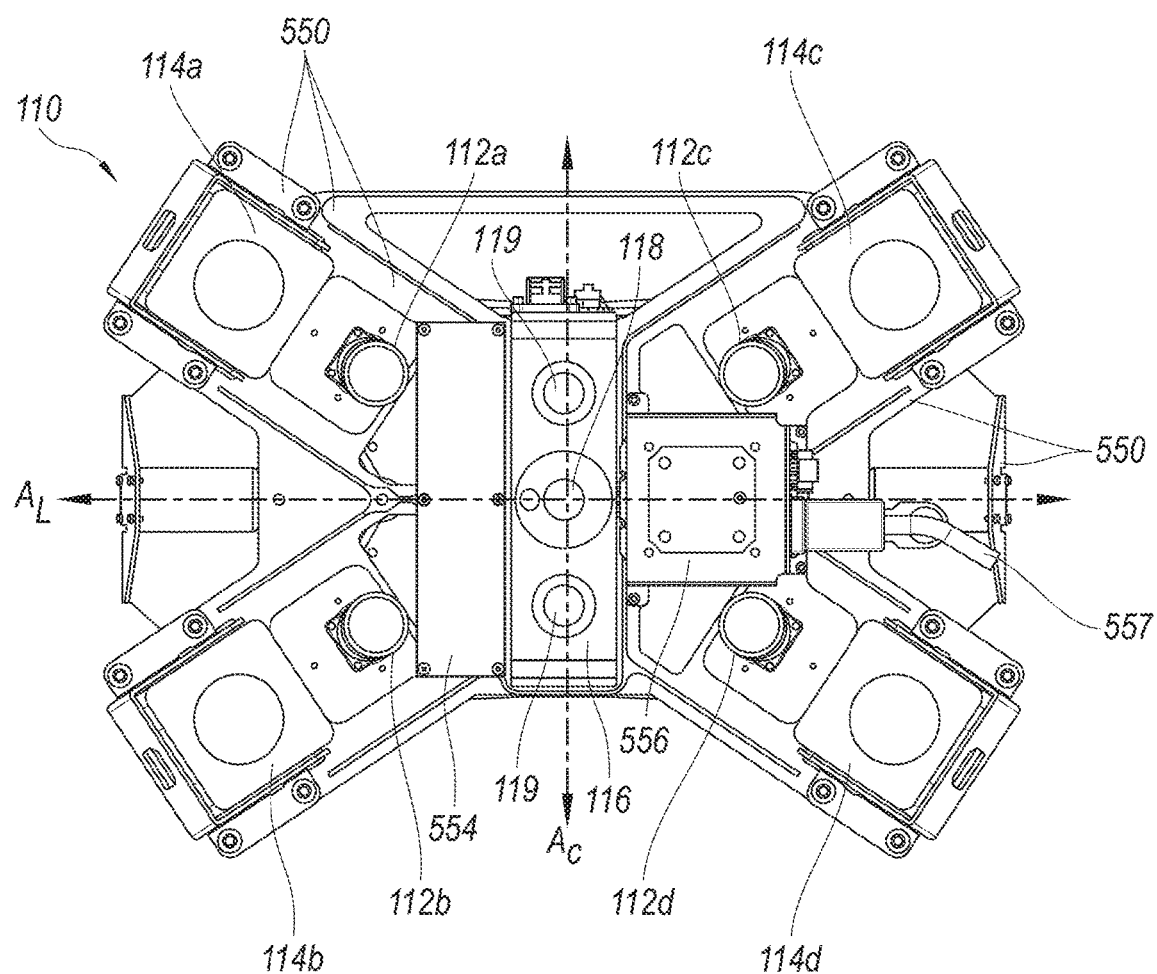
Figure 5C:
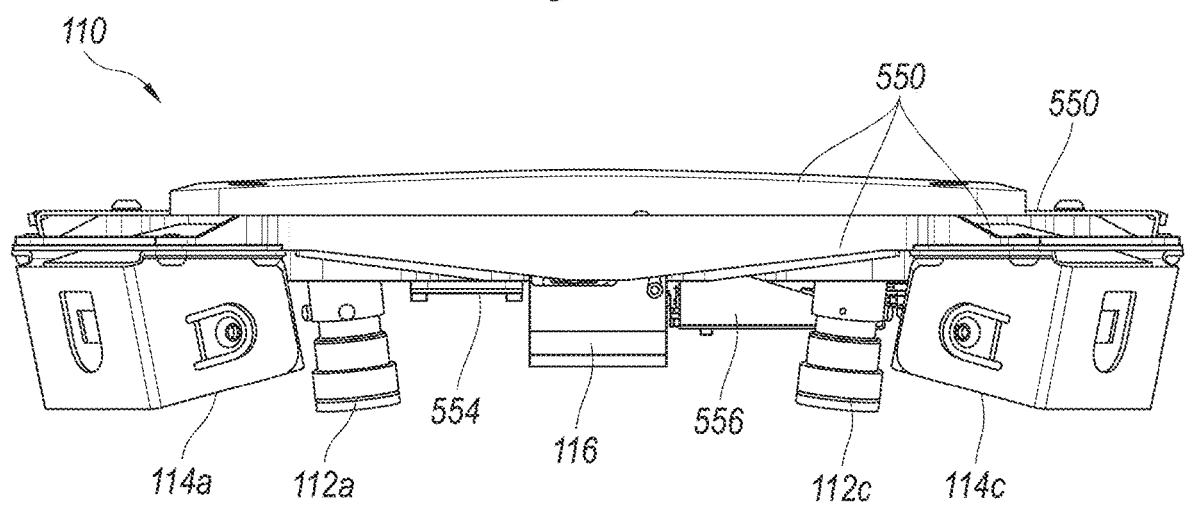

FIGS. 4A-4C are an isometric view, a bottom view, and a side view, respectively, of the camera array 110 in accordance with embodiments of the present technology. Referring to FIGS. 4A-4C together, the camera array 110 includes a housing 440 (e.g., a shell, casing, etc.) that encloses the various components of the camera array 110. FIGS. 5A-5C are an isometric view, a bottom view, and a side view, respectively, of the camera array 110 with the housing 440 removed in accordance with embodiments of the present technology.

Referring to FIGS. 5A-5C together, the camera array 110 includes a support structure such as a frame 550, and the cameras 112 (identified individually as first through fourth cameras 112a-112d), the trackers 114 (identified individually as first through fourth trackers 114a-114d), and the depth sensor 116 are coupled (e.g., attached, securely mounted, etc.) to the frame 550. The frame 550 can be made of metal, composite materials, or other suitably strong and rigid materials. The cameras 112, the trackers 114, and the depth sensor 116 can be coupled to the frame via bolts, brackets, adhesives, and/or other suitable fasteners. In some embodiments, the frame 550 is configured to act as a heat sink for the cameras 112, the trackers 114, and/or other electronic components of the camera array 110 and can, for example, uniformly distribute heat around the camera array 110 with minimal thermally-induced deflection/deformation.

In the illustrated embodiment, the depth sensor 116—including the projector 118 and a pair of the cameras 119—is coupled to a central (e.g., radially-inward) portion of the frame 550 and is generally aligned along a central axis $A_C$ (FIG. 5B) of the frame 550. In one aspect of the present technology, positioning the depth sensor 116 at/near the center of the camera array 110 can help ensure that the scene 108 (FIG. 1) is adequately illuminated by the projector 118 for depth estimation during operation.

The cameras 112 and the trackers 114 can be distributed about the frame 550 radially outward from the depth sensor 116. In some embodiments, the trackers 114 are mounted to the frame radially outward of the cameras 112. In the illustrated embodiment, the cameras 112 and the trackers 114 are positioned symmetrically/equally about the frame 550. For example, each of the cameras 112 and the trackers 114 can be equally spaced apart from (i) the central axis $A_C$ and (ii) a longitudinal axis $A_L$ extending perpendicular to the central axis $A_C$. In one aspect of the present technology, this spacing can simplify the processing performed by the processing device 102 (FIG. 1) when synthesizing the output image corresponding to the virtual camera perspective of the scene 108, as described in detail above. In another aspect of the present technology, the arrangement of the cameras 112 generally maximizes the disparity of the cameras 112 which can help facilitate depth estimation using image data from the cameras 112. In other embodiments, the camera array 110 can include more or fewer of the cameras 112 and/or the trackers 114, and/or the cameras 112 and the trackers 114 can be arranged differently about the frame 550.

In the illustrated embodiment, the cameras 112 and the trackers 114 are oriented/angled inward toward the central portion of the frame 550 (e.g., toward the axes $A_C$ and $A_L$). In other embodiments, the frame 550 can be configured (e.g., shaped, angled, etc.) to orient the cameras 112 and the trackers 114 inward without requiring that the cameras 112 and the trackers 114 be angled relative to the frame 550. In some embodiments, the cameras 112 can generally focus on a first focal point in the scene 108, and the trackers 114 can also generally focus on a second focal point in the scene 108 that can be different or the same as the first focal point of the cameras 112. In some embodiments, a field of view of each of the cameras 112 can at least partially overlap the field of view of one or more other ones of the cameras 112, and a field of view of each of the trackers 114 can at least partially overlap the field of view of one or more of the other ones of the trackers 114. In some embodiments, the field of view of individual ones of the cameras 112 can be selected (e.g., via selection of an attached lens) to vary the effective spatial resolution of the cameras 112. For example, the field of view of the cameras 112 can be made smaller to increase their effective spatial resolution and the resulting accuracy of the system 100.

In the illustrated embodiment, the cameras 112 are identical—for example, having the same focal length, focal depth, resolution, color characteristics, and other intrinsic parameters. In other embodiments, some or all the cameras 112 can be different. For example, the first and second cameras 112a, b (e.g., a first pair of the cameras 112) can have different focal lengths of other characteristics than the third and fourth cameras 112c, d (e.g., a second pair of the cameras 112). In some such embodiments, the system 100 can render/generate a stereoscopic view independently for each pair of the cameras 112. In some embodiments, the cameras 112 can have a resolution of about 10 megapixels or greater (e.g., 12 megapixels or greater). In some embodiments, the cameras 112 can have relatively small lenses compared to typical high-resolution cameras (e.g., about 50 millimeters).

Referring to FIGS. 4A-5C together, the housing 440 includes a lower surface 442 having (i) first openings 444 aligned with the cameras 112, (ii) second openings 446 aligned with the trackers 114, and (iii) a third opening 448 aligned with the depth sensor 116. In some embodiments, some or all the openings 444, 446, 448 can be covered with transparent panels (e.g., glass or plastic, panels) to inhibit ingress of dust, contaminations, etc., into the camera array 110. In some embodiments, the housing 440 is configured (e.g., shaped) such that the transparent panels across each of the openings 444, 446, 448 are arranged perpendicular to the angle of the cameras 112, trackers 114, and the depth sensor 116 to, for example, reduce distortion in the capture data resulting from reflection, diffraction, scattering, etc., of light passing through the panels.

Referring again to FIGS. 5A-5C together, the camera array 110 can include integrated electrical components, communication components, and/or other components. In the illustrated embodiment, for example, the camera array 110 further includes a circuit board 554 (e.g., a printed circuit board) and an in/out (I/O) circuitry box 556 coupled to the frame 550. The I/O circuitry box 556 can be used to communicatively couple the cameras 112, the trackers 114, and/or the depth sensor 116 to other components of the system 100, such as the processing device 102, via one or more connectors 557 (FIG. 5B).

Figure 6:
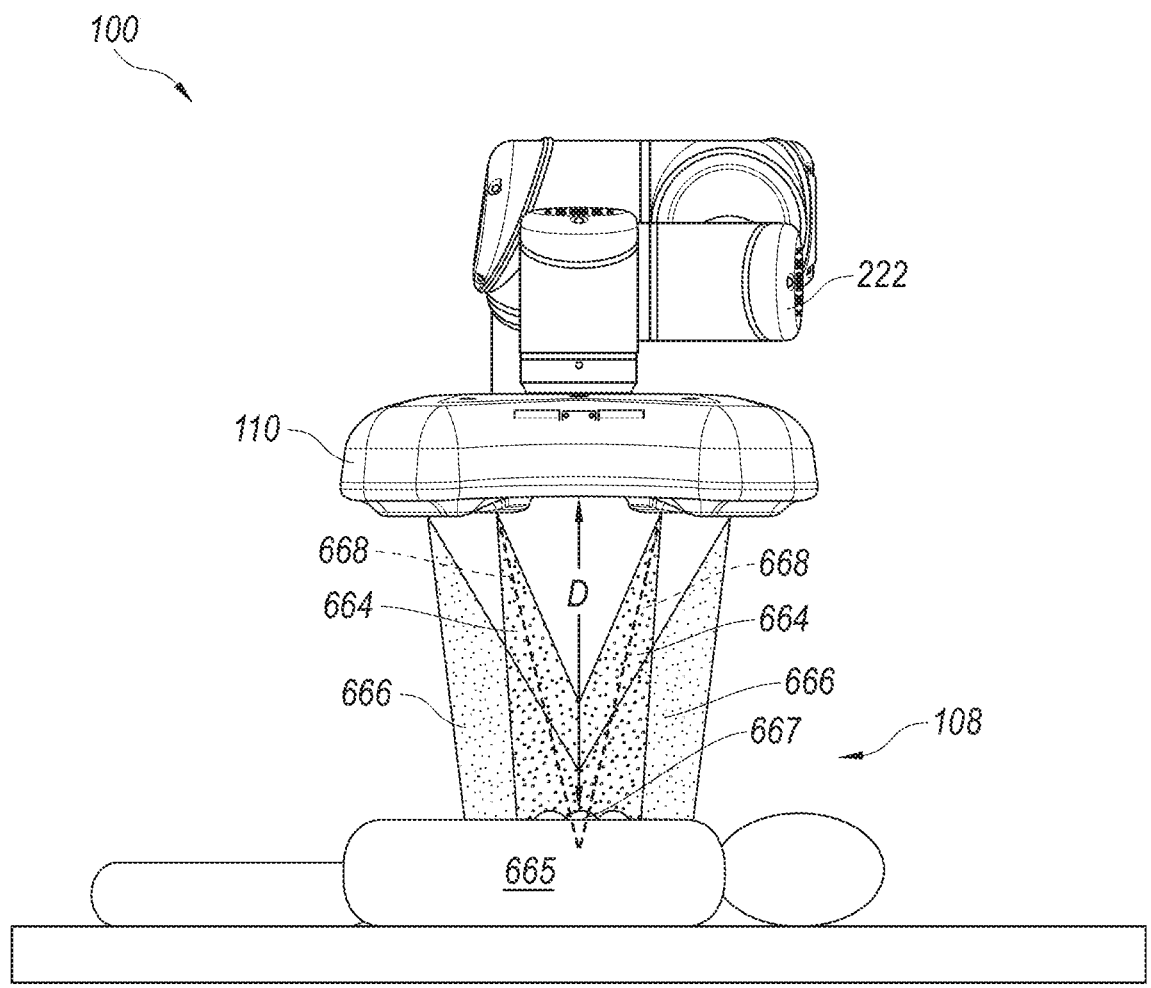
FIG. 6 is a front view of the imaging system in a surgical environment during a surgical application in accordance with embodiments of the present technology.

FIG. 6 is a front view of the system 100 in a surgical environment during a surgical application in accordance with embodiments of the present technology. In the illustrated embodiment, a patient 665 is positioned at least partially within the scene 108 below the camera array 110. The surgical application can be a procedure to be carried out on a portion of interest of the patient, such as a spinal procedure to be carried out on a spine 667 of the patient 665. The spinal procedure can be, for example, a spinal fusion procedure. In other embodiments, the surgical application can target another portion of interest of the body of the patient 665.

Referring to FIGS. 3A-6 together, in some embodiments the camera array 110 can be moved into position above the patient 665 by articulating/moving one or more of the joints 332 and/or the elongate portions 334 of the arm 222. In some embodiments, the camera array 110 can be positioned such that the depth sensor 116 is generally aligned with the spine 677 of the patient (e.g., such that the spine 677 is generally aligned with the central axis $A_C$ of the camera array 110). In some embodiments, the camera array 110 can be positioned such that the depth sensor 116 is positioned at a distance D above the spine 677 of the patient 665 that corresponds to the main focal depth/plane of the depth sensor 116. In some embodiments, the focal depth D of the depth sensor is about 75 centimeters. In one aspect of the present technology, this positioning of the depth sensor 116 can ensure accurate depth measurement that facilitates accurate image reconstruction of the spine 667.

In the illustrated embodiment, the cameras 112 each have a field of view 664 of the scene 108, and the trackers 114 each have a field of view 666 of the scene 108. In some embodiments, the fields of view 664 of the cameras 112 can at least partially overlap one another to together define an imaging volume. Likewise, the fields of view 666 of the trackers 114 can at least partially overlap one another (and/or the fields of view 664 of the cameras 112) to together define a tracking volume. In some embodiments, the trackers 114 are positioned such that the overlap of the fields of view 666 is maximized, and the tracking volume is defined as the volume in which all the fields of view 666 overlap. In some embodiments, the tracking volume is larger than the imaging volume because (i) the fields of view 666 of the trackers 114 are larger than the fields of view 664 of the cameras 112 and/or (ii) the trackers 114 are positioned farther radially outward along the camera array 110 (e.g., nearer to a perimeter of the camera array 110). For example, the fields of view 666 of the trackers 114 can be about 82×70 degrees, whereas the fields of view 664 of the cameras 112 can be about 15×15 degrees. In some embodiments, the fields of view 666 of the cameras 112 do not fully overlap, but the regions of overlap are tiled such that the resulting imaging volume covered by all the cameras 112 has a selected volume that exists as a subset of the volume covered by the trackers 114. In some embodiments, each of the cameras 112 has a focal axis 668, and the focal axes 668 generally converge at a point below the focal depth D of the depth sensor 116 (e.g., at a point about five centimeters below the focal depth D of the depth sensor 118). In one aspect of the present technology, the convergence/alignment of the focal axes 668 can generally maximize disparity measurements between the cameras 112. In another aspect of the present technology, the arrangement of the cameras 112 about the camera array 110 provides for high angular resolution of the spine 667 of the patient 665 that enables the processing device 102 to reconstruct a virtual image of the scene 108 including the spine 667.

III. Selected Embodiments of High Precision Object Tracking

Referring again to FIG. 1, the system 100 is configured to track one or more objects within the scene 108—such as the tip 103 of the tool 101—via (i) an optical-based tracking method using the trackers 114 and/or (ii) an image-based tracking method using the cameras 112. For example, the processing device 102 (e.g., the tracking processing device 109) can process data from the trackers 114 to determine a position (e.g., a location and orientation) of the markers 105 in the scene 108. More specifically, the processing device 102 can triangulate the three-dimensional (3D) location of the markers 105 from images taken by multiple ones of the trackers 114. Then, the processing device 102 can estimate the location of the tip 103 of the tool based on a known (e.g., predetermined, calibrated, etc.) model of the tool 101 by, for example, determining a centroid of the constellation of the markers 105 and applying a known offset between the centroid and the tip 103 of the tool 101. In some embodiments, the trackers 114 operate at a wavelength (e.g., near infrared) such that the markers 105 are easily identifiable in the images from the trackers 114—greatly simplifying the image processing necessary to identify the location of the markers 105.

However, to track a rigid body such as the tool 101, at least three markers 105 must be attached so that the system 100 can track the centroid of the constellation of markers 105. Often, due to practical constraints, the multiple markers 105 must be placed opposite the tip 103 of the tool 101 (e.g., the working portion of the tool 101) so that they remain visible when the tool 101 is grasped by a user and do not interfere with the user. Thus, the known offset between the markers 105 and the tip 103 of the tool 101 must be relatively great so that the markers 105 remain visible, and any error in the determined position of the markers 105 will be propagated along the length of the tool 101.

Additionally or alternatively, the processing device 102 can process image data (e.g., visible-wavelength data) from the cameras 112 to determine the position of the tool 101. Such image-based processing can achieve relatively higher accuracy than optical-based methods using the trackers 114, but at lower framerates due to the complexity of the image processing. This is especially true for high-resolution images, such as those captured by the cameras 112. More specifically, the cameras 112 are configured to capture high-frequency details of the surface of the scene 108 that act as feature points that are characteristic of the tracked object. However, there tends to be an overabundance of image features that must be filtered to reduce false correspondences that degrade tracking accuracy—further increasing computational requirements.

In some embodiments, the system 100 is configured to track the tip 103 of the tool 101 with high precision and low latency by using tracking information from both the trackers 114 and the cameras 112. For example, the system 100 can (i) process data from the trackers 114 to estimate a position of the tip 103, (ii) define regions of interest (ROIs) in images from the cameras 112 based on the estimated position, and then (iii) process the ROIs in the images to determine the position of the tip 103 with greater precision than the estimated position from the trackers 114 (e.g., with sub-pixel accuracy). In one aspect of the present technology, the image processing on the ROIs is computationally inexpensive and fast because the ROIs comprise only a small portion of the image data from the cameras 112.

Figure 7:
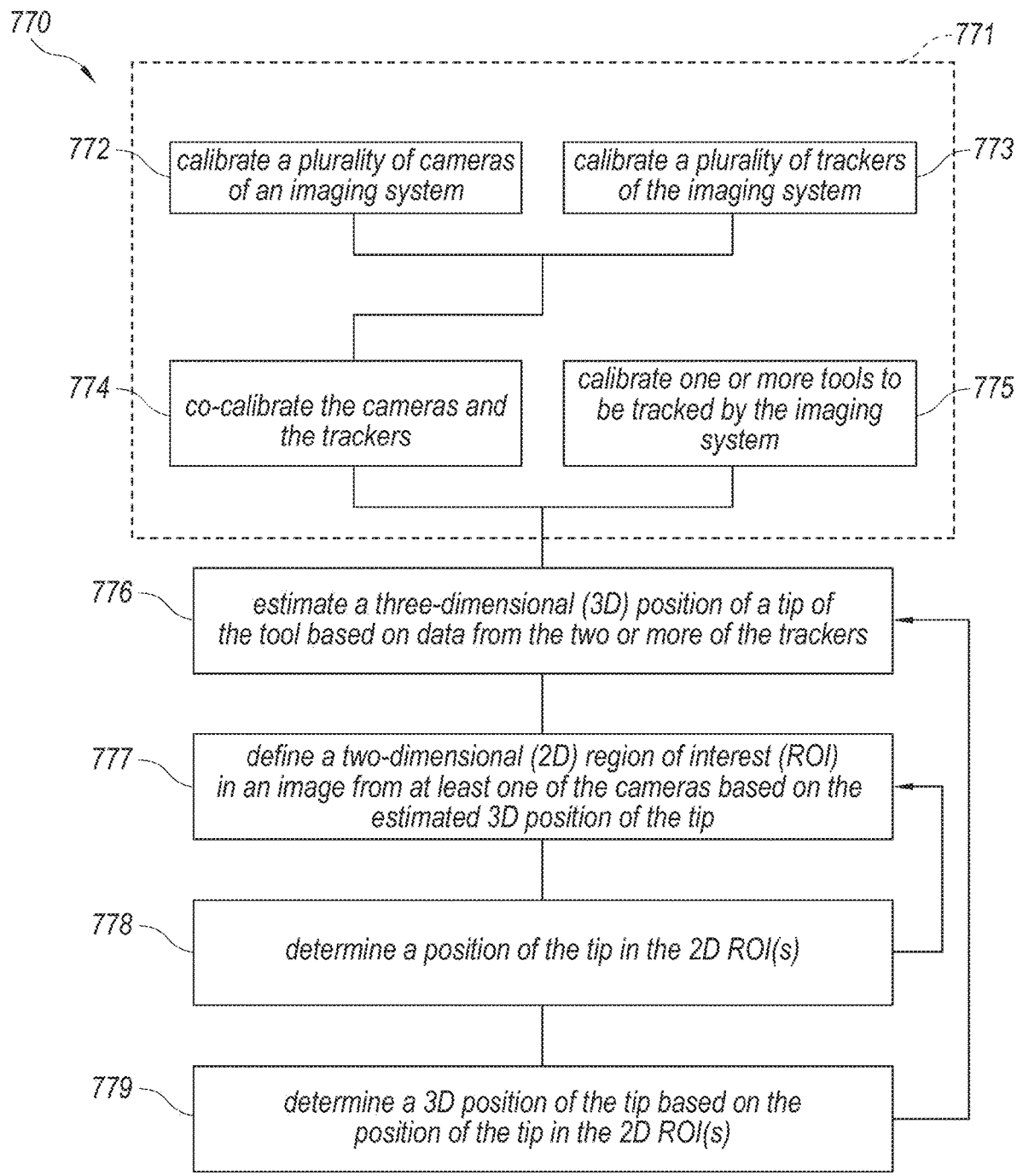
FIG. 7 is a flow diagram of a process or method for tracking a tip of a tool using the imaging system in accordance with embodiments of the present technology.

More specifically, FIG. 7 is a flow diagram of a process or method 770 for tracking the tip 103 of the tool 101 using tracking/positional data captured by the trackers 114 and image data captured by the cameras 112 in accordance with embodiments of the present technology. Although some features of the method 770 are described in the context of the embodiments shown in FIGS. 1-6 for the sake of illustration, one skilled in the art will readily understand that the method 770 can be carried out using other suitable systems and/or devices described herein. Similarly, while reference is made herein to tracking of the tool 101, the method 770 can be used to track all or a portion of other objects within the scene 108 (e.g., an arm of a surgeon, additional tools, etc.) including reflective markers.

At block 771, the method 770 includes calibrating the system 100 both intrinsically and extrinsically and calibrating the parameters of the tool 101 to enable accurate tracking of the tool 101. In the illustrated embodiment, the calibration includes blocks 772-775. At blocks 772 and 773, the method 770 includes calibrating the cameras 112 and the trackers 114 of the system 100, respectively. In some embodiments, for the cameras 112 and the trackers 114, the processing device 102 performs a calibration process to detect the positions and orientation of each of the cameras 112/trackers 114 in 3D space with respect to a shared origin and/or an amount of overlap in their respective fields of view. For example, in some embodiments the processing device 102 can (i) process captured images from each of the cameras 112/trackers 114 including a fiducial marker placed in the scene 108 and (ii) perform an optimization over the camera parameters and distortion coefficients to minimize reprojection error for key points (e.g., points corresponding to the fiducial markers). In some embodiments, the processing device 102 can perform a calibration process by correlating feature points across different cameras views. The correlated features can be, for example, reflective marker centroids from binary images, scale-invariant feature transforms (SIFT) features from grayscale or color images, etc. In some embodiments, the processing device 102 can extract feature points from a ChArUco target and process the feature points with the OpenCV camera calibration routine. In other embodiments, such a calibration can be performed with a Halcon circle target or other custom target with well-defined feature points with known locations. In some embodiments, further calibration refinement can be carried out using bundle analysis and/or other suitable techniques.

Figure 8:
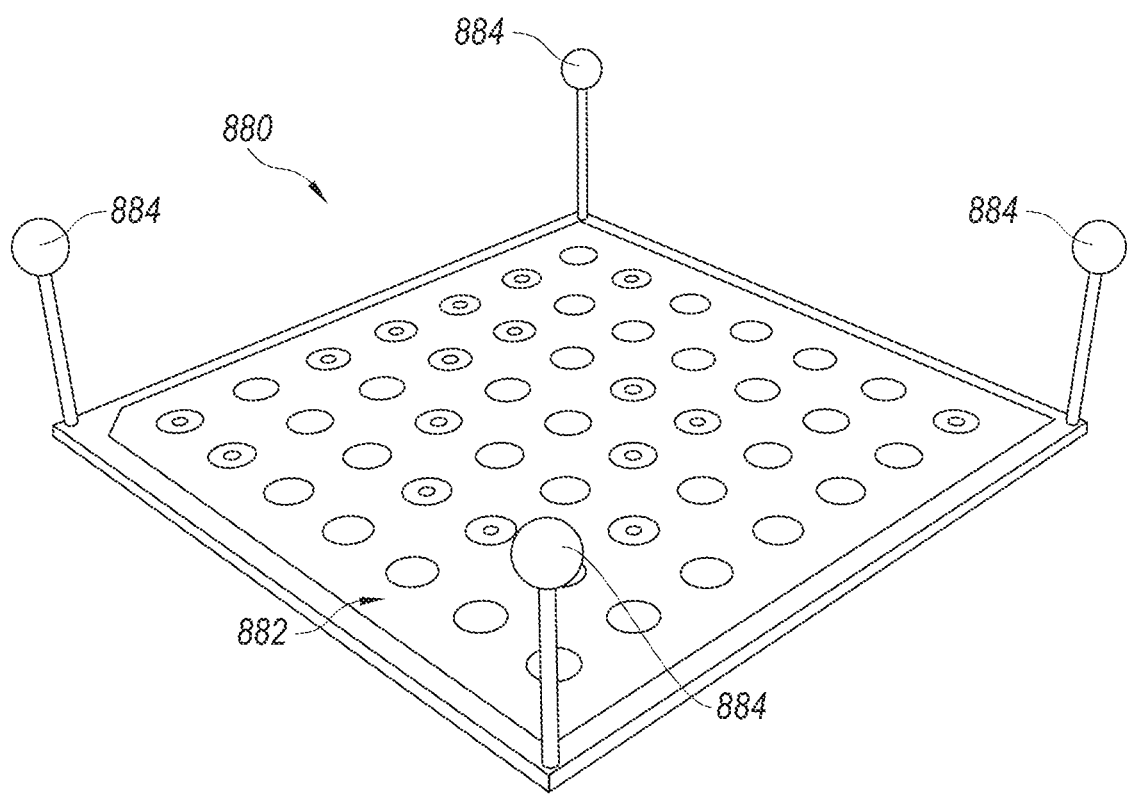
FIG. 8 is an isometric view of a co-calibration target for use in calibrating the imaging system in accordance with embodiments of the present technology.

At block 774, the method 770 includes co-calibrating the cameras 112 and the trackers 114 such that data from both can be used to track the tool 101 in a common reference frame. In some embodiments, the cameras 112 and the trackers 114 can be co-calibrated based on imaging of a known target in the scene 108. FIG. 8, for example, is an isometric view of a co-calibration target 880 in accordance with embodiments of the present technology. In some embodiments, the spectral sensitivity of the cameras 112 and the trackers 114 does not overlap. For example, the cameras 112 can be visible wavelength cameras and the trackers 114 can be infrared imagers. Accordingly, in the illustrated embodiment the target 880 is a multispectral target that includes (i) a pattern 882 that is visible to the cameras 112 and (ii) a plurality of retroreflective markers 884 that are visible to the trackers 114. The pattern 882 and the markers 884 share a common origin and coordinate frame such that the cameras 112 and the trackers 114 can be co-calibrated to measure positions (e.g., of the tool 101) in the common origin and coordinate frame. That is, the resulting extrinsic co-calibration of the cameras 112 and the trackers 114 can be expressed in a common reference frame or with a measured transform between their reference origins. In the illustrated embodiment, the pattern 882 is a printed black and white Halcon circle target pattern. In other embodiments, the pattern 882 can be another black and white (or other high contrast color combination) ArUco, ChArUco, or Halcon target pattern.

In other embodiments, the target 880 as measured by the cameras 112 and the trackers 114 does not have to be precisely aligned and can be determined separately using a hand-eye calibration technique. In yet other embodiments, the ink or material used to create the two high contrast regions of the pattern 882 can exhibit similar absorption/reflection to the measurement wavelengths used for both the cameras 112 and the trackers 114. In some embodiments, blocks 772-774 can be combined into a single calibration step based on imaging of the target 880 where, for example, the target 880 is configured (e.g., shaped, sized, precisely manufactured, etc.) to allow for calibration points to be uniformly sampled over the desired tracking volume.

At block 775, the method 770 includes calibrating the tool 101 (and/or any additional objects to be tracked) to determine the principal axis of the tool 101 and the position of the tip 103 relative to the attached constellation of the markers 105. In some embodiments, calibration of the system 100 (block 771) need only be performed once so long as the cameras 112 and the trackers 114 remain spatially fixed (e.g., rigidly fixed to the frame 550 of the camera array 110) and their optical properties do not change. However, vibration and/or thermal cycling can cause small changes in the optical properties of the cameras 112 and the trackers 114. In such instances, the system 100 can be recalibrated.

Figure 9A:
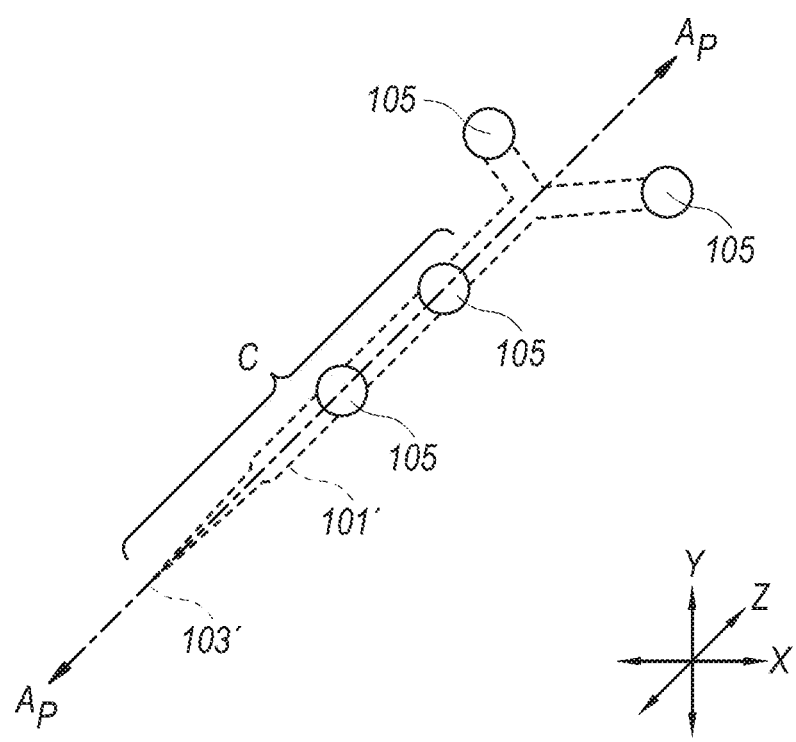
FIGS. 9A and 9B are partially schematic side views of the tool illustrating various steps of the method of FIG. 7 in accordance with embodiments of the technology.
Figure 9B:
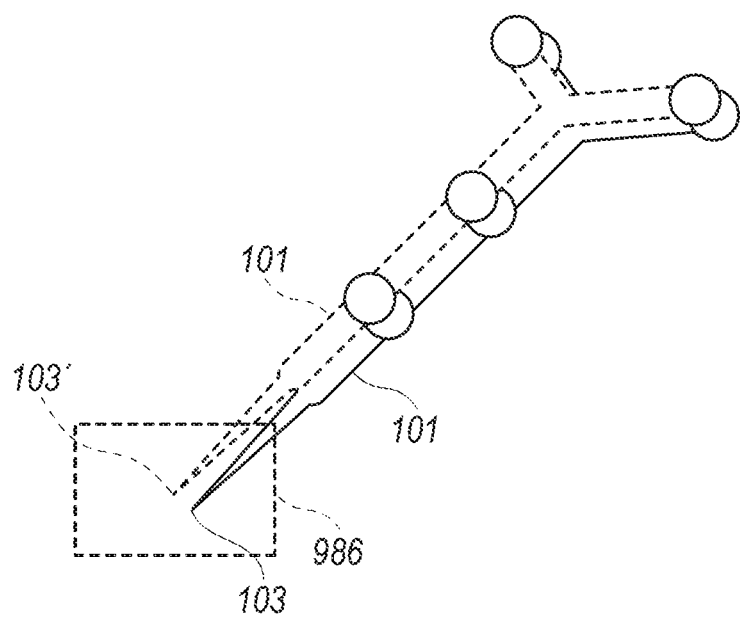

Blocks 776-779 illustrate the processing steps to determine the position of the tip 103 of the tool 101 within the scene 108 with high precision and low latency. FIGS. 9A and 9B are partially schematic side views of the tool 101 illustrating various steps of the method 770 of FIG. 7 in accordance with embodiments of the technology. Accordingly, some aspects of the method 770 are described in the context of FIGS. 9A and 9B.

At block 776, the method 770 includes estimating a 3D position of the tip 103 of the tool 101 using the trackers 114. For example, the trackers 114 can process the captured image data to determine a centroid of the markers 105 in the image data. The processing device 102 can (i) receive the centroid information from the trackers 114, (ii) triangulate the centroid information to determine 3D positions of the markers 105, (iii) determine the principal axis of the tool 101 based on the calibration of the tool 101 (block 775), and then (iv) estimate the 3D position of the tip 103 based on the principal axis and the calibrated offset of the tip 103 relative to the markers 105. For example, as shown in FIG. 9A, the system 100 estimates the position and orientation of the tool 101 (shown in dashed lines as tool position 101'; e.g., relative to a Cartesian XYZ coordinate system) based on the determined/measured locations of the markers 105, and models the tool 101 as having a principal axis $A_P$. Then, the system 100 estimates a position of the tip 103 (shown as tip position 103') based on a calibrated offset C from the markers 105 (e.g., from a centroid of the markers 105) along the principal axis $A_P$. Data from at least two of the trackers 114 is needed so that the position of the markers 105 can be triangulated from the positional data. In some embodiments, the system 100 can estimate the position of the tip 103 using data from each of the trackers 114. In other embodiments, the processing carried out to estimate the 3D position of the tip 103 can be divided differently between the trackers 114 and the processing device 102. For example, the processing device 102 can be configured to receive the raw image data from the trackers and to determine the centroid of the markers in the image data.

At block 777, the method 770 includes defining a region of interest (ROI) in an image from one or more of the cameras 112 based on the estimated position of the tip 103 determined at block 776. As shown in FIG. 9B, for example, the system 100 can define a ROI 986 around the estimated 3D tip position 103'. More specifically, the estimated 3D tip position 103' is used to initialize a 3D volume (e.g., a cube, sphere, rectangular prism, etc.) with a determined critical dimension (e.g., radius, area, diameter, etc.). The 3D volume is then mapped/projected to the 2D images from the cameras 112. In some embodiments, the critical dimension can be fixed based on, for example, a known geometry of the system 100 and motion parameters of the tool 101. As further shown in FIG. 9B, the actual 3D position of the tip 103 of the tool 101 can differ from the estimated position of the tip 103' due to measurement errors (e.g., that are propagated along the length of the tool 101). In some embodiments, the dimensions and/or shape of the ROI 986 are selected such that the actual position of the tip 103 will always or nearly always fall within the ROI 986. In other embodiments, the system 100 can initially define the ROI 986 to have a minimum size, and iteratively expand the size of the ROI 986 until the position of the tip 103 is determined to be within the ROI 986, as described in detail below with reference to block 778.

In some embodiments, the ROI processing can be carried out for data from only one of the cameras 112, such as one of the cameras 112 specifically positioned to capture images of the tool 101. In other embodiments, the ROI processing can be carried out for more than one (e.g., all) of the cameras 112 in the camera array 110. That is, ROIs can be defined in one or more images from each of the cameras 112.

At block 778, the method 770 includes determine a position of the tip 103 of the tool 101 in the ROI(s). In some embodiments, the processing device 102 can determine the position of the tip 103 by identifying a set of feature points directly from the ROI image using a scale-invariant feature transform (SIFT) method, speeded up robust features (SURF) method, and/or oriented FAST and rotated BRIEF (ORB) method. In other embodiments, the processing device 102 can use a histogram to localize the position of the tip 103 in the ROI(s). In yet other embodiments, the processing device 102 can (i) determine/identify the principal axis of the tool 101 using, for example, a Hough transform or principal components analysis (PCA), and then (ii) search along the principal axis for the position of the tip 103 using, for example, a method using feature points or the image gradient (e.g., the Sobel filter) to determine the tip location along the principal axis of the tool 101. In yet other embodiments, the processing device 102 can utilize a gradient-based approach that allows for sub-pixel localization of the tip 103.

Finally, at block 779, the determined position(s) of the tip 103 in the ROI(s) is used to determine an updated/refined 3D position of the tip 103 that is, for example, more precise than the position estimated by the trackers 114 at block 776. In some embodiments, where the system 100 processes image data from multiple ones of the cameras 112 (e.g., where ROIs are determined in images from multiple ones of the cameras 112), the 3D position of the tip 103 can be directly triangulated based on the determined positions of the tip 103 in the 2D images from the cameras 112. In other embodiments, where the system 100 processes image data from only one of the cameras 112 (e.g., where a ROI is determined in an image from only one of the cameras 112), the 3D position of the tip 103 can be determined by projecting the position of the tip 103 in the 2D image from the camera 112 into a 3D line using the calibration of the camera 112 (block 772). In some embodiments, the system 100 then determines the position of the tip 103 as the closest point or intersection of (i) this 3D line defined by the tip position in the camera image and (ii) the principal axis $A_P$ (FIG. 9A) determined from the trackers 114 (block 776) and the calibration of the tool 101 (block 775).

In one aspect of the present technology, the system 100 can determine the updated 3D position of the tip 103 with higher precision by processing image data from multiple ones of the cameras 112 rather than from just one of the cameras 112. In particular, by utilizing multiple ones of the cameras 112, the refined 3D position of the tip 103 is determined directly by triangulation and does not rely on data from the trackers 114 (e.g., the position and orientation of the principal axis $A_P$). In another aspect of the present technology, utilizing multiple ones of the cameras 112 provides increased flexibility in the layout/positioning of the camera array 110 as the relative orientation between the camera array 110 and the tool 101 is not restricted so long as the tool 101 is visible by at least two of the cameras 112.

In another aspect of the present technology, the position of the tip 103 determined from the cameras 112 (block 779) is more precise than the position determined from the trackers 114 (block 776) because the cameras 112 have a higher resolution than the trackers 114, which can cover a larger field of view than the cameras 112 but with lower resolution. Moreover, the trackers 114 typically work well if the markers 105 are imaged with enough pixels and with a sharp edge between the markers 105 and the background of the scene 108. However, the cameras 112 can have a very high resolution such that they cover a similar field of view as the trackers 114, but with much higher effective spatial resolution.

In some embodiments, after determining the 3D position of the tip 103, the system 100 can overlay a graphical representation of the tool 101 onto a virtual rendering of the scene 108 (e.g., as provided on the display device 104). The method 770 can further return to block 776 to update the 3D position of the tool 101 in real-time or near-real time with high precision. In one aspect of the present technology, the updating can be done at a high framerate and with low latency because only the ROIs in the image data from the cameras 112 need to be processed—rather than the entire images—because the 3D estimate of the position of the tip 103 from the trackers 114 is used to initialize the ROIs. Without using the ROIs, the processing requirements for the images from the cameras 112 would be very large and would be difficult or impossible to process with low latency.

Alternatively, the resolution of the cameras 112 could be lowered to reduce the processing requirements, but the resulting system would provide little to no accuracy improvement over the trackers 114 alone.

IV. Additional Examples

The following examples are illustrative of several embodiments of the present technology:

1. A camera array, comprising:
   a support structure having a center;
   a depth sensor mounted to the support structure proximate to the center;
   a plurality of cameras mounted to the support structure radially outward from the depth sensor, wherein the cameras are configured to capture image data of a scene; and
   a plurality of trackers mounted to the support structure radially outward from the cameras, wherein the trackers are configured to capture positional data of a tool within the scene.

2. The camera array of example 1 wherein the plurality of cameras includes four cameras, wherein the plurality of trackers includes four trackers, and wherein the cameras and the trackers are positioned symmetrically about the support structure.

3. The camera array of example 1 or example 2 wherein the support structure includes a central axis and a longitudinal axis extending orthogonal to the central axis, wherein the depth sensor is aligned along the central axis, and wherein each of the cameras and each of the trackers are equally spaced apart from the central axis and the longitudinal axis.

4. The camera array of any one of examples 1-3 wherein the trackers are infrared imagers.

5. The camera array of any one of examples 1-4 wherein the trackers are imagers having a different spectral sensitivity than the cameras.

6. The camera array of any one of examples 1-5 wherein the cameras and the trackers each have a field of view, wherein the fields of view of the cameras at least partially overlap to define an imaging volume, and wherein the fields of view of the trackers at least partially overlap to define a tracking volume that is larger than the imaging volume.

7. The camera array of any one of examples 1-6 wherein the cameras are each angled radially inward toward the center of the support structure.

8. The camera array of example 7 wherein the depth sensor has a focal plane, wherein the cameras each have a focal axis, and wherein the focal axes of the cameras converge at a point below the focal plane of the depth sensor.

9. A mediated-reality system, comprising:
   a camera array including—
     a support structure having a center;
     a depth sensor mounted to the support structure proximate to the center;
     a plurality of cameras mounted to the support structure radially outward from the depth sensor, wherein the cameras are configured to capture image data of a scene; and
     a plurality of trackers mounted to the support structure radially outward from the cameras, wherein the trackers are configured to capture positional data of a tool within the scene;
   an input controller configured to control a position and orientation of a virtual perspective of the scene;

a processing device communicatively coupled to the camera array and the input controller, wherein the processing device is configured to—
  synthesize a virtual image corresponding to the virtual perspective based on the image data from at least two of the cameras; and
  determine a position of the tool based on the positional data from at least two of the trackers; and
a display device communicatively coupled to the processing device, wherein the display device is configured to display a graphical representation of the tool at the determined position in the virtual image.

10. The mediated-reality system of example 9 wherein the processing device is further configured to determine the position of the tool based on the image data from at least one of the cameras.

11. The mediated-reality system of example 10 wherein the processing device is configured to determine the position of the tool by—
  estimating an initial three-dimensional (3D) position of the tool based on the positional data from the at least two of the trackers;
  defining a region of interest in the image data from the at least one of the cameras based on the initial 3D position of the tool;
  processing the image data in the region of interest to determine a position of the tool in the region of interest; and
  determining an updated 3D position of the tool based on the determined position of the tool in the region of interest.

12. A method of imaging a subject within a scene, the method comprising:
  aligning a depth sensor of a camera array with a portion of interest of the subject such that the portion of interest is positioned proximate a focal depth of the depth sensor;
  capturing, with a plurality of cameras of the camera array, image data of the scene including the portion of interest of the subject;
  capturing, with a plurality of trackers of the camera array, positional data of a tool within the scene;
  receiving input regarding a selected position and orientation of a virtual perspective of the scene;
  synthesizing a virtual image corresponding to the virtual perspective of the scene based on the image data;
  determining a position of the tool based on the positional data; and
  displaying, at a display device, a graphical representation of the tool at the determined position in the virtual image.

13. The method of example 12 wherein the scene is a surgical scene, and wherein the portion of interest of the subject is a spine of the subject.

14. The method of example 12 or example 13 wherein the cameras each have a focal axis, and wherein the focal axes of the cameras converge at a point below the focal depth of the depth sensor.

15. The method of any one of examples 12-14 wherein determining the position and orientation of the tool is further based on the image data.

16. The method of example 15 wherein determining the position of the tool includes—
  estimating an initial three-dimensional (3D) position of the tool based on the positional data;
  defining one or more regions of interest in the image data based on the initial 3D position of the tool;
  processing the image data in the one or more regions of interest to determine a position of the tool in the one or more regions of interest; and
  determining an updated 3D position of the tool based on the determined position of the tool in the one or more regions of interest.

17. A method for determining the position of a tip of a tool within a scene, the method comprising:
  receiving positional data of the tool from at least two trackers;
  estimating a three-dimensional (3D) position of the tip of the tool based on the positional data;
  receiving an image of the scene from each of one or more cameras;
  for the image from each of the one or more cameras—
    defining a region of interest in the image based on the estimated 3D position of the tip of the tool; and
    processing the image in the region of interest to determine a position of the tip of the tool in the region of interest; and
  determining an updated 3D position of the tip of the tool based on the determined position of the tool in the region of interest of the one or more images.

18. The method of example 17 wherein receiving the image from each of the one or more cameras includes receiving images from corresponding ones of a plurality of cameras, and wherein determining the updated 3D position of the tip of the tool includes triangulating the updated 3D position based on the determined positions of the tip of the tool in the regions of interest in the images from the plurality of cameras.

19. The method of example 17 or example 18 wherein estimating the 3D position of the tip of the tool includes—
  determining a primary axis of the tool; and
  estimating the 3D position based on a known offset along the primary axis.

20. The method of example 19 wherein receiving the image from each of the one or more cameras includes receiving an image from one camera, and wherein determining the updated 3D position of the tip of the tool includes—
  projecting the position of the tip of the tool in the region of interest into a 3D line based on a calibration of the camera; and
  determining the updated 3D position of the tip of the tool based on an intersection of the 3D line and the primary axis of the tool.

V. Conclusion

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A camera array, comprising:
   a support structure having a central region;
   a depth sensor mounted to the support structure at the center;
   a plurality of cameras mounted to the support structure outward from the depth sensor away from the central region, wherein the cameras are configured to capture image data of a scene; and
   a plurality of trackers mounted to the support structure outward from the cameras away from the central region, wherein the trackers are configured to capture positional data of a tool within the scene.

2. The camera array of claim 1 wherein the plurality of cameras includes four cameras, wherein the plurality of trackers includes four trackers, and wherein the cameras and the trackers are positioned symmetrically about the support structure.

3. The camera array of claim 1 wherein the support structure includes a central axis and a longitudinal axis extending orthogonal to the central axis, wherein the depth sensor is aligned along the central axis, and wherein each of the cameras and each of the trackers are equally spaced apart from the central axis and the longitudinal axis.

4. The camera array of claim 1 wherein the trackers are infrared imagers.

5. The camera array of claim 1 wherein the trackers are imagers having a different spectral sensitivity than the cameras.

6. The camera array of claim 1 wherein the cameras and the trackers each have a field of view, wherein the fields of view of the cameras at least partially overlap to define an imaging volume, and wherein the fields of view of the trackers at least partially overlap to define a tracking volume that is larger than the imaging volume.

7. The camera array of claim 1 wherein the cameras are each angled radially inward toward the central region of the support structure.

8. A camera array, comprising:
   a support structure having a center,
   a depth sensor mounted to the support structure proximate to the center, wherein the depth sensor has a focal plane;
   a plurality of cameras mounted to the support structure radially outward from the depth sensor, wherein the cameras are configured to capture image data of a scene,
   wherein the cameras each have a focal axis, and wherein the focal axes of the cameras converge at a point below the focal plane of the depth sensor, and
   a plurality of trackers mounted to the support structure radially outward from the cameras,
   wherein the trackers are configured to capture positional data of a tool within the scene.

9. A mediated-reality system, comprising:
   a camera array including
   a support structure having a central region;
   a depth sensor mounted to the support structure at the central region;
   a plurality of cameras mounted to the support structure outward from the depth sensor away from the central region, wherein the cameras are configured to capture image data of a scene; and
   a plurality of trackers mounted to the support structure radially outward from the cameras away from the central region, wherein the trackers are configured to capture positional data of a tool within the scene;
   an input controller configured to control a position and orientation of a virtual perspective of the scene;
   a processing device communicatively coupled to the camera array and the input controller, wherein the processing device is configured to synthesize a virtual image corresponding to the virtual perspective based on the image data from at least two of the cameras; and determine a position of the tool based on the positional data from at least two of the trackers; and
   a display device communicatively coupled to the processing device, wherein the display device is configured to display a graphical representation of the tool at the determined position in the virtual image.

10. The mediated-reality system of claim 9 wherein the processing device is further configured to determine the position of the tool based on the image data from at least one of the cameras.

11. The mediated-reality system of claim 10 wherein the processing device is configured to determine the position of the tool by
    estimating an initial three-dimensional (3D) position of the tool based on the positional data from the at least two of the trackers;
    defining a region of interest in the image data from the at least one of the cameras based on the initial 3D position of the tool;
    processing the image data in the region of interest to determine a position of the tool in the region of interest; and d
    determining an updated 3D position of the tool based on the determined position of the tool in the region of interest.

12. A method of imaging a subject within a scene, the method comprising:
    aligning a depth sensor with a portion of interest of the subject such that the portion of interest is positioned proximate a focal depth of the depth sensor;
    capturing, with a plurality of cameras, image data of the scene including the portion of interest of the subject;
    capturing, with a plurality of trackers, positional data of a tool within the scene, wherein the depth sensor, the cameras, and the trackers are commonly mounted to a support structure of a camera array;

receiving input regarding a selected position and orientation of a virtual perspective of the scene;

synthesizing a virtual image corresponding to the virtual perspective of the scene based on the image data;

determining a position of the tool based on the positional data; and displaying, at a display device, a graphical representation of the tool at the determined position in the virtual image.

13. The method of claim 12 wherein the scene is a surgical scene, and wherein the portion of interest of the subject is a spine of the subject.

14. The method of claim 12 wherein determining the position and orientation of the tool is further based on the image data.

15. The method of claim 14 wherein determining the position of the tool includes estimating an initial three-dimensional (3D) position of the tool based on the positional data; defining one or more regions of interest in the image data based on the initial 3D position of the tool; processing the image data in the one or more regions of interest to determine a position of the tool in the one or more regions of interest; and determining an updated 3D position of the tool based on the determined position of the tool in the one or more regions of interest.

16. A method of imaging a subject within a scene, the method comprising:

aligning a depth sensor of a camera array with a portion of interest of the subject such that the portion of interest is positioned proximate a focal depth of the depth sensor;

capturing, with a plurality of cameras of the camera array, image data of the scene including the portion of interest of the subject, wherein the cameras each have a focal axis, and wherein the focal axes of the cameras converge at a point below the focal depth of the depth sensor capturing, with a plurality of trackers of the camera array, positional data of a tool within the scene, receiving input regarding a selected position and orientation of a virtual perspective of the scene;

synthesizing a virtual image corresponding to the virtual perspective of the scene based on the image data;

determining a position of the tool based on the positional data; and displaying, at a display device, a graphical representation of the tool at the determined position in the virtual image.

17. A method for determining a position of a tip of a tool within a scene, the method comprising:

receiving positional data of the tool from at least two trackers mounted to the camera array; estimating a three-dimensional (3D) position of the tip of the tool based on the positional data;

receiving an image of the scene from each of one or more cameras mounted to the camera array;

for the image from each of the one or more cameras defining a region of interest in the image based on the estimated 3D position of the tip of the tool; and processing the image in the region of interest to determine a position of the tip of the tool in the region of interest; and determining an updated 3D position of the tip of the tool based on the determined position of the tool in the region of interest of the one or more images.

18. The method of claim 17 wherein receiving the image from each of the one or more cameras includes receiving images from corresponding ones of a plurality of cameras, and wherein determining the updated 3D position of the tip of the tool includes triangulating the updated 3D position based on the determined positions of the tip of the tool in the regions of interest in the images from the plurality of cameras.

19. The method of claim 17 wherein estimating the 3D position of the tip of the tool includes determining a primary axis of the tool; and estimating the 3D position based on a known offset along the primary axis.

20. A method for determining a position of a tip of a tool within a scene, the method comprising:

receiving positional data of the tool from at least two trackers;

estimating a three-dimensional (3D) position of the tip of the tool based on the positional data;

receiving an image from one camera;

for the image from the camera defining a region of interest in the image based on the estimated 3D position of the tip of the tool; and processing the image in the region of interest to determine a position of the tip of the tool in the region of interest; and determining an updated 3D position of the tip of the tool based on the determined position of the tool in the region of interest of the image by projecting the position of the tip of the tool in the region of interest into a 3D line based on a calibration of the camera; and determining the updated 3D position of the tip of the tool based on an intersection of the 3D line and the primary axis of the tool.

* * * * *